United States Patent [19]

Tritsch

[11] 4,084,592
[45] Apr. 18, 1978

[54] DISPOSABLE PREFOLDED DIAPER WITH PERMANENTLY ATTACHED ADHESIVE CLOSURE SYSTEM

[75] Inventor: Ludwig Tritsch, Wilmette, Ill.

[73] Assignee: Johnson & Johnson, New Brunswick, N.J.

[21] Appl. No.: 539,554

[22] Filed: Jan. 8, 1975

[51] Int. Cl.² .................................................. A61F 13/16
[52] U.S. Cl. .................................... 128/287; 128/284
[58] Field of Search ........... 128/287, 286, 284, 290 R; 24/67, 73 A

[56] References Cited

U.S. PATENT DOCUMENTS

| | | | |
|---|---|---|---|
| 3,180,335 | 4/1965 | Duncan et al. | 128/287 |
| 3,620,217 | 11/1971 | Gellert | 128/284 |
| 3,638,651 | 2/1972 | Torr | 128/284 |
| 3,642,001 | 2/1972 | Sabee | 128/287 |
| 3,776,234 | 12/1973 | Hoey | 128/287 |
| 3,800,796 | 4/1974 | Jacob | 128/287 |
| 3,840,013 | 10/1974 | Mesek et al. | 128/284 |
| 3,848,597 | 11/1974 | Endres | 128/287 |
| 3,862,634 | 1/1975 | Small | 128/284 |
| 3,874,386 | 4/1975 | Kozak | 128/287 |
| 3,875,621 | 4/1975 | Karami | 24/67 |
| 3,880,165 | 4/1975 | Prizzia | 128/284 |
| 3,921,638 | 11/1975 | Schaar | 128/287 |

*Primary Examiner*—John D. Yasko

[57] ABSTRACT

A disposable diaper is provided with adhesive tabs permanently adhered to a backing sheet of a diaper at marginal locations. Each tab is folded back on itself so that a tacky surface on the free end of each tab is exposed. A release coated surface is provided on the backing sheet of the diaper inwardly of the folded over free end of each tab so that when each side margin of the diaper is folded along the length of the diaper prior to packaging, the exposed tacky surface of the free end of the tab is lightly adhered to the release coated surface to hold the diaper in a folded attitude and to retain the tacky surface in a protected position within the confines of the fold, thereby eliminating the need for a separate release sheet. For use, the tacky surfaces adhered to the respective release surfaces are exposed for applying the diaper to the baby by merely unfolding the diaper.

12 Claims, 9 Drawing Figures

U.S. Patent April 18, 1978 Sheet 1 of 2 4,084,592
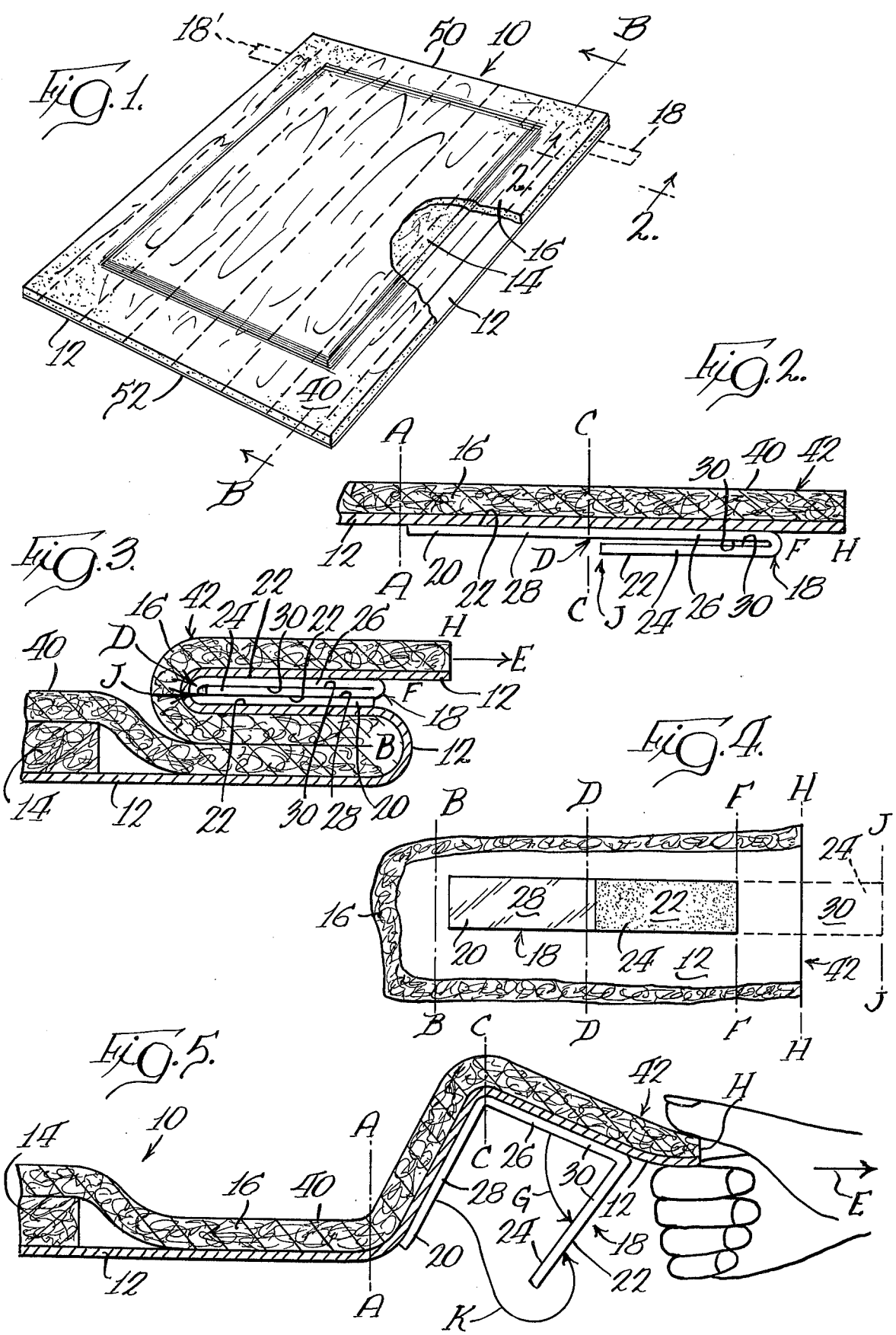

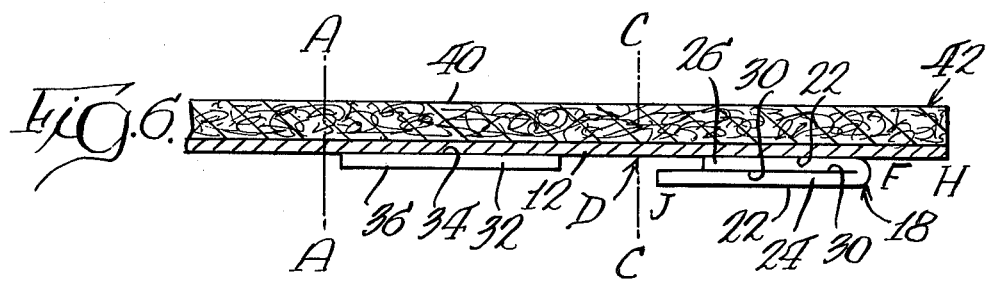
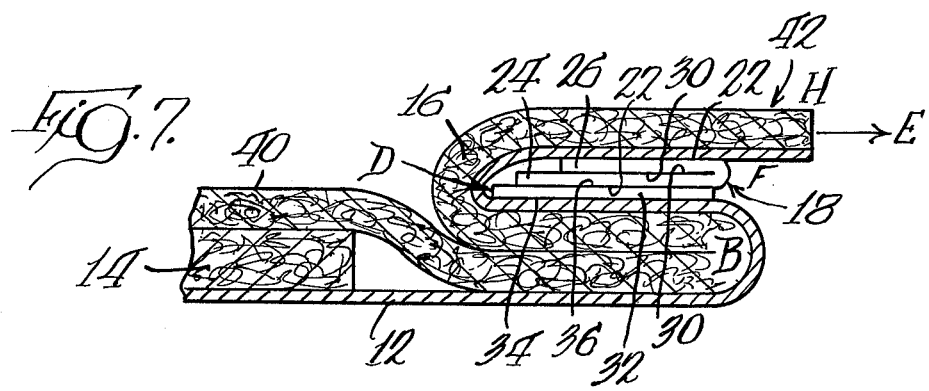
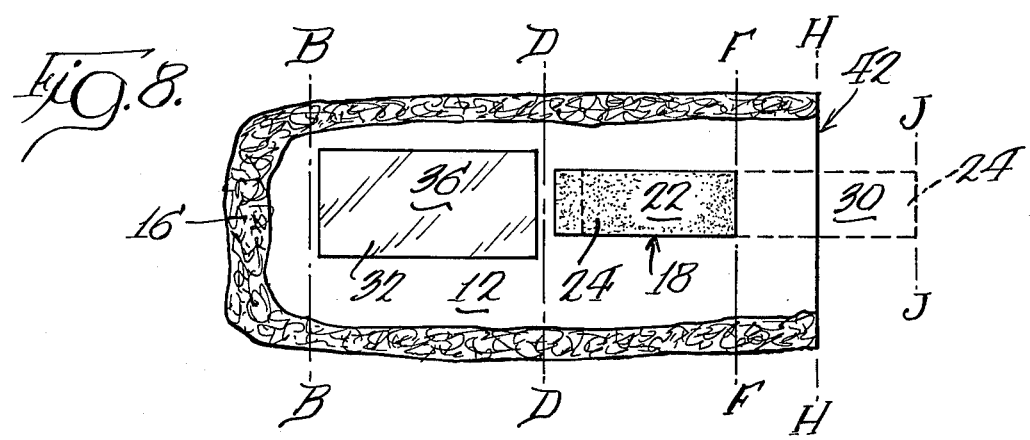
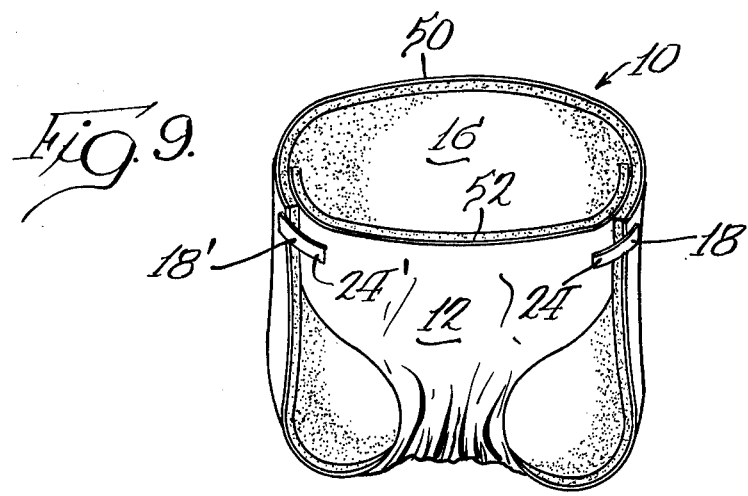

DISPOSABLE PREFOLDED DIAPER WITH PERMANENTLY ATTACHED ADHESIVE CLOSURE SYSTEM

BACKGROUND OF THE INVENTION

Disposable diapers provide substantial advantages in convenience over diapers intended to be laundered and reused, particularly when the diapers are used away from home. In recent years, many different disposable diapers have been proposed and some have been successful in the marketplace. Typical disposable diaper structures comprise a facing material to be brought into contact with the infant's skin, an absorptive moisture-retaining layer of relatively high moisture-holding capacity, and a moisture-impervious backing sheet. Typical disposable diaper structures are shown in U.S. Pat. No. 3,612,055 to Mesek et al., and in U.S. Pat. No. Re. 26,151 to Duncan et al.

As may be seen from the above-cited patents, it has been desirable to obviate the problems that are inherent in closure systems utilizing extraneous fasteners such as safety pins, snaps and zippers, and tab-type adhesive closure systems have been used in lieu of such extraneous fasteners.

The adhesive systems shown in the above-mentioned patents include adhesive tabs which are adhered to the backing sheet and which extend outwardly from opposite sides of the diaper at one end thereof. The exposed areas of the adhesive tabs are provided with cover strips thereon that are readily separable from the adhesive tabs. However, disposable diapers using an adhesive closure system of this general type have the disadvantage in that the consumer must dispose of the cover strips when they are separated from the adhesive strips. This is an inconvenience to the consumer who is placing the diaper on a baby at about the same time.

An illustrative prior art adhesive system having cover strips permanently attached to the diaper is shown in Gellert U.S. Pat. No. 3,646,937. The Gellert arrangement has the disadvantage of having a release surface on the inside of the diaper, where it can possibly come in contact with a baby's tender skin. The closure system illustrated in the Gellert patent also has the disadvantage that it requires the use of two hands to peel back the releasable end of the adhesive tape. Additional disadvantages are the complexities and expense which are added to the manufacturing process because each adhesive closure has to be manipulated on the front side, around the edge, and on the back side of the diaper, instead of handling it on one side only.

SUMMARY OF THE INVENTION

In this invention, the side of the diaper that faces away from the baby when the diaper is in use is provided with adhesive tabs which do not require cover strips. The tabs are adhered to the diaper at marginal locations and are folded inwardly upon themselves so that a tacky surface on a free end of each tab is exposed and faces in the same direction as the diaper backing sheet. A release coated region is provided on the diaper inwardly of and adjacent to the folded-over free end of each tab so that when each side margin of the diaper is folded along the length of the diaper, the tacky surface of the free end of each tab is releasably adhered to the release coated region. This holds the diaper in a folded attitude suitable for storage or packaging, yet in an attitude from which it can be opened by a lateral pull which simultaneously releases the free end of the adhesive tab ready for use in applying the diaper to an infant. Thus, the adhesive tabs of the diaper are readily made available for use and nothing need be disposed of. Also, the tacky surfaces ultimately used to secure the diaper are covered and positioned in a protected location within the confines of the folded diaper prior to use.

In one embodiment of this invention, a release coated surface is provided on the side of the adhesive tab opposite from the tacky side thereof, and the tab is folded inwardly about fold lines which divide the tab into three substantially equal segments so that the terminal tab segments overlie the central tab segment. Thus, when a box pleat is formed in the diaper, the tacky surface of the free end of the tape tab is positioned in surface-to-surface releasable engagement with the release coating on the tab segment adhesively attached to the diaper. This particular embodiment has the advantage that the entire closure system is provided by a single relatively long adhesive tab, the major portion of the length of the tab adhesive being adhered to the diaper to increase the strength of the bond between the tab and the diaper as compared to prior art closure systems.

In an alternate embodiment, the release coating is separate from the tab and can be on a separate member adhesively secured to the diaper backing sheet inwardly of the adhesive tab. In this embodiment the tab is folded about its mid-portion so that the tacky surface on the tab free end is disposed in surface-to-surface releasable engagement with the release coated surface on the separate member when a pleat is formed in the diaper. The release coated surface can be larger in area than the tape tab, thereby making alignment of the tacky surface on the tab free end and the release region less critical during manufacture of the diapers.

In either embodiment, the need for a separate release strip covering the adhesive surface is eliminated, yet the adhesive surface is completely protected within the confines of the folded diaper to prevent undesired inadvertent adherence prior to application of the diaper to a baby. The tabs are made readily available for use by merely opening the folded end of the diaper to overcome the light adhesion between the free ends of the tabs and the release surfaces.

BRIEF DESCRIPTION OF THE DRAWINGS

FIG. 1 is a perspective view, partly broken away, of an open unfolded diaper in accordance with one embodiment of this invention with a phantom showing of the adhesive tabs in extended position;

FIG. 2 is an enlarged fragmentary cross sectional elevation taken along plane 2—2 in FIG. 1;

FIG. 3 is an enlarged fragmentary cross sectional elevation similar to FIG. 2 and showing the diaper after folding in its storage position;

FIG. 4 is a fragmentary bottom plan view of FIG. 2 with a phantom showing of tab in extended position;

FIG. 5 is a fragmentary sectional elevation illustrating one embodiment of the invention as the adhesive tab is about to reach readiness for use;

FIG. 6 is a fragmentary cross sectional elevation similar to FIG. 2 and illustrating an alternate embodiment of the invention;

FIG. 7 is a fragmentary cross sectional elevation of the embodiment shown in FIG. 6, illustrating the diaper configuration after folding in storage position;

FIG. 8 is a fragmentary bottom plan view of FIG. 6 with a phantom showing of the adhesive tab in extended position; and FIG. 9 is a perspective view on a reduced scale and showing a diaper in a configuration assumed after the diaper is placed on an infant.

DESCRIPTION OF THE PREFERRED EMBODIMENTS

While this invention is susceptible of embodiment in many different forms, there is shown in the drawings and will herein be described in detail preferred embodiments of the invention, with the understanding that the present disclosure is to be considered as an exemplification of the principles of the invention and is not intended to limit the invention to the embodiments illustrated.

Referring to the drawings, diaper 10, shown fully opened and laid out flat in FIG. 1, includes moisture-impervious backing sheet 12 which forms a diaper outside surface for direction away from an infant. Facing sheet 16 forms an inside surface for direction toward an infant, is made of moisture-pervious fibrous material and is substantially equal in dimension and coterminous with backing sheet 12. While not critical to the present invention, diaper 10 also preferably includes highly moisture-absorbent fibrous pad or batt 14 situated between backing sheet 12 and facing sheet 16. Pad 14 is also rectangular in shape, but smaller than the facing and backing sheets and is centrally disposed therebetween. Pad or batt 14 may be formed in accordance with the teachings set forth in commonly assigned U.S. Pat. No. 3,612,055 to Mesek et al.

As illustrated in FIGS. 2–5, substantially identical adhesive tabs 18 and 18' are located at opposite longitudinal sides of the diaper near one end thereof and are used to secure the diaper on the baby. Tabs 18 and 18' are provided with a tacky, pressure-sensitive surface such as surface 22 on tab 18, along the entire length of each tab. In this embodiment the adhesive tape segment forming tab 18 is divided into three portions of substantially equal length: fixed end portion 20, central portion 26, and free end portion 24 at the distal end of tab 18. Central portion 26 and free end portion 24 have face 30 situated opposite tacky surface 22. For manufacturing expedience, preferably entire face 30 is provided with a release coating. Fixed end portion 20 has release coated surface 28 on the face opposite tacky surface 22 and provides a release region on backing sheet 12. Central portion 26 and fixed end portion 20 of tab 18 are permanently adhered to the plastic backing sheet 12 of diaper 10 at a marginal location thereon; however, central portion 26 can also remain unattached, if desired.

During manufacture and storage, side margins of diaper 10 are folded toward each other with backing sheet 12 innermost so that adhesive tabs 18 and 18' are situated within the resulting fold. That is, free end portion 24 of tab 18 is folded over upon central portion 26 and is releasably attached to release surface 28 by folding longitudinal margin 42 of diaper 10 so as to bring tacky surface 22 in juxtaposition with release surface 28. Longitudinal or side margin 42 of diaper 10 can also be further folded over upon itself about line B—B with backing sheet 12 on the outside, resulting in tab 18 being repositioned as shown in FIG. 3. Line B—B is a line formed by the intersection of plane A—A in FIG. 2 with the plane of diaper 10 and is usually positioned about ⅛ inch to about ½ inch inwardly from fixed end 20.

Plane A—A is substantially perpendicular to diaper 10 and to outside surface 40 of facing layer 16. To form a box pleat as shown in FIG. 3, margin 42 is further folded upon itself about line D—D, with backing sheet 12 on the inside. Line D—D is a line formed by the intersection of plane C—C (FIG. 2) with the plane of diaper 10. Plane C—C usually is situated about ⅛ inch to about ½ inch inwardly from folded over free end portion 24 and is substantially perpendicular to diaper 10 and to non-tacky surface 30 of tab 18. FIG. 3 shows diaper 10 in its folded over position, forming a box pleat and with tacky surface 22 of folded over free end portion 24 releasably adhered to release surface 28 on fixed end portion 20. Diaper 10 can be packaged and stored in this position until ready for use.

It is recognized that the order of the folding operations can be changed, and the same result will be achieved, thus different orders of folding are considered to be within the spirit and scope of this invention.

As described hereinabove, the folds preferably are made about a line spaced about ⅛ inch to about ½ inch from the terminal portions of tab 18 in order to compensate for the thickness of the several layers of the diaper 10 and the tab 18. However, the folding planes and fold lines shown in the drawings are only approximations since the overall thickness of the materials being folded will vary depending on the particular materials that are employed in any given instance.

In an alternate embodiment, illustrated in FIGS. 6–8, the tape segment forming adhesive tab 18 is divided into two approximately equal portions, that is, permanently adhered or fixed end 26 and free end 24, which portions are substantially the same as the respective portions in the embodiment shown in FIGS. 2–5. The embodiment of FIGS. 6–8 differs from the embodiment of FIGS. 2–5 in that separate tape segment 32 carries the release coating. Tape segment 32 has tacky face 34 permanently adhered to diaper 10 at a location inwardly disposed from fixed end 26 of tab 18 and opposite face 36 which bears a release coating for protecting the tacky surface 22 on tab free end 24. Separate tape member 32 is disposed substantially on the longitudinal axis of tab 18. In lieu of separate tab member 32, a suitable release coating can be provided on backing sheet 12, if desired.

FIG. 7 shows a diaper provided with the tab construction shown in FIG. 6 in its folded over position. Tacky surface 22 of folded over free end 24 is releasably adhered to release surface 36 on tape member 32, and the diaper can be stored in this position until ready for use.

In the folded positions illustrated in FIGS. 3 and 7, tacky surface 22 on free end 24 is protected. However, tacky surface 22 can be readily exposed by gripping side margin 42 of diaper 10, and pulling outwardly in the direction indicated by arrow E. As best shown in FIGS. 4 and 5, tacky surface 22 on free end 24 readily separates from the release coated surface 28 (in the embodiment shown in FIGS. 2–5) or release surface 36 (in the embodiment shown in FIGS. 6–8) with which it is in releasable contact, and the diaper will unfold to its rectangular shape and will be ready for use. Arrow K indicates the path of tacky surface 22 on free end 24 as it is separated from releasable adherence to release surface 28. Arrow G indicates the path of uncoated surface 30 when free end portion 24 is displaced from juxtaposition with central portion 26. Upon release from surface 28, free end 24 can be grasped and can subsequently be pressed against an adjacent portion of the backing sheet 12 so as to secure diaper 10 on a baby.

Adhesive tab 18 preferably is made of a resilient material that does not retain the folded over position indicated in FIGS. 2 and 6 after the diaper 10 is unfolded from the position indicated in FIGS. 3 and 7. Rather, upon release, folded over end portion 24 will rotate about line F—F in the direction indicated by arrow G in FIG. 5, and will tend to assume a position substantially along the longitudinal axis of tab 18, thus free end 24 can be easily grasped for securing diaper 10 to a baby.

If adhesive tab 18 is made of a material that tends to retain its folded over position after the diaper is unfolded, then the consumer unfolds free end portion 24 from central portion 26 by sliding a fingernail beneath the distal portion of the free end 24, grasping free end 24, and then rotating it about line F—F in the direction indicated by arrow G. Since free end 24 is not adhered to central portion 26, and since these two portions merely have their uncoated faces 30 in juxtaposition with each other, no resistance is encountered when free end 24 is unfolded.

This invention has the advantage of providing an adhesive closure means which is permanently attached to the diaper and in which no components of the closure system need to be disposed of by the consumer when the diaper is applied to a baby. Another advantage is that the release coated surface on the fixed portion of the tab remains on the outside part of the diaper, where it is out of contact with the baby's tender skin, after the tacky surface on the free end of the tab is exposed. A feature of this invention is that each side of the diaper can be unfolded and the tacky free end of the adhesive tab thereby exposed by using only one hand, leaving the user's other hand free for other purposes. A further advantage of this invention is that the entire adhesive closure means is on only one side of the diaper, thus simplifying the manufacturing process.

When a single adhesive tab is used, having a tacky free end, a central portion, and a fixed portion which is adhered to the diaper on one face, and having an opposite face with a release coated surface, the need for a separate cover strip is eliminated. Also, the relatively long adhesive surface which is in contact with the diaper increases the overall strength of the bond.

When a release surface separate from the adhesive tab is used as shown in FIGS. 6–8, the release area or region can be made wider than the tacky portion of the tab, thereby making alignment of the tacky adhesive and the release area less critical during diaper manufacture.

If desired, tacky surface 22 can be omitted on part of the free end portion 24. As best illustrated in FIGS. 3 and 7, a short length of the tacky surface 22 at the juncture of central portion 26 and free end portion 24 is neither adhered to the plastic backing sheet 12 nor releasably adhered to release coated surface 28 (FIG. 3) or release coated surface 36 (FIG. 7). A pressure sensitive adhesive can be omitted along this short section which is adjacent to line F—F, if desired. Further, as can be seen from FIGS. 2, 4, 6 and 8, the sections of tacky surface 22 between lines F—F and H—H on free end portion 24 (FIG. 8) are in contact with the plastic backing sheet 12 when free end 24 is unfolded, and only the sections of tacky surface 22 between lines H—H and J—J on end portion 24 are actually adhered to an adjacent portion of plastic backing sheet 12 when securing diaper 10 on a baby. Thus, although that section of the tacky surface 22 between lines F—F and H—H on free end 24 contacts backing sheet 12 adjacent to central portion 26 when free end 24 is unfolded and provides a stronger adherence between tab 18 and the backing sheet 12, tacky surface 22 is not required on this section of free end 24 and can be omitted if desired.

A suitable backing sheet material for the diaper embodying the present invention can be an opaque polyethylene web about 0.001 inch thick. Another suitable sheet material for this purpose is a polyethylene terephthalate web having a thickness of about 0.0005 inch.

Several different types of facing materials may be used for diaper facing sheet 16. For example, facing sheet 16 may be made up of a mixture of fibers consisting predominantly of inexpensive short cellulosic fibers, such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$, is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 16 may also be made of an apertured, nonwoven fabric which is formed, for example, in accordance with the teachings in commonly assigned U.S. Pat. Nos. 2,862,251; 3,081,514; and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers or blends thereof. Typical facing layers made of a polyester-type material can have a weight of $\frac{3}{4}$ oz./yd.$^2$.

In addition, facing sheet 16 can be formed of a nonapertured material, such as a nonwoven isotropic web, sponge, or the like. In all of the aforementioned facings, the materials should be relatively hydrophobic so as to retard wicking within the facing layer.

Highly moisture-absorbent fibrous pad or batt 14 which is substantially rectangular in shape, but usually smaller than the facing and backing sheet, is centrally disposed therebetween. Pad 14 can be formed in accordance with the teachings of U.S. Pat. No. 3,612,055 to Mesek et al. Alternatively, a higher moisture-absorbent layer can be provided substantially coextensive with backing sheet 12 if desired.

Typical disposable diapers which can be fitted with a tab-type fastener described hereinabove are shown in U.S. Pat. No. 3,612,055 to Mesek et al. and in U.S. Pat. No. 3,683,916 to Mesek et al. Other suitable disposable diaper structures are shown in U.S. Pat. No. Re. 26,151 to Duncan et al.

Release properties can be imparted to the release regions such as surface 28 and surface 36 by coating these surfaces with a silicone release compound, or the like. Appropriate release formulations suitable for this purpose are well known in the art.

The pressure-sensitive adhesive coating for providing tacky surface 22 is formed by applying a pressure-sensitive adhesive known in the art to the appropriate tab surface. The applied adhesive shall have good tack, good cohesive strength, good resistance to moisture and good resistance to aging. Illustrative of such adhesives are mixtures of natural or synthetic rubber, zinc oxide, and various resins, also latices of natural or synthetic rubber, or water dispersions of acrylic tacky polymers or copolymers.

Diaper 10 is applied to an infant by positioning diaper ends 50 and 52 around the waist of the infant with the intermediate portion of diaper 10 being disposed in the infant's crotch. Free end portions 24 and 24' of respective tabs 18 and 18' are then separated from their release areas and diaper ends 50 and 52 are pulled into a tight fitting engagement with the infant's waist. The exposed portion of the tacky surface on tabs 18 and 18' is then pressed against an adjacent portion of plastic backing sheet 12 to secure the diaper on the infant. The final configuration assumed by the diaper is shown in perspective on a reduced scale in FIG. 9, and the diaper is held in this position by the adhesive closure system of the present invention.

I claim:

1. A disposable diaper, comprising:
    an absorbent pad assembly having a front surface, a back surface, a pair of side edges, a longitudinally extending central panel, and panel means overlying the front surface of the central panel adjacent its sides, said panel means including a pair of longitudinally extending outermost panels defining the side edges of the pad assembly;
    a pair of pressure-sensitive tape strips having a first portion fixedly secured to the back surface of said outermost panels adjacent the side edges of the pad assembly and a second securement portion extending from an end of the first portions adjacent the side edges of the pad assembly for use in securing the diaper about an infant during placement of the diaper; and
    release sheet means positioned on the pad assembly at a location on another panel to cover adhesive on the securement portions of the strips, said securement portions of the strips being attached to the release sheet means to retain the outermost pleats in their overlying relationship prior to placement of the diaper.

2. The diaper of claim 1 wherein the pad assembly has a plurality of longitudinally extending folds defining the central panel, a pair of first panels extending from and overlying the front surface of the central panel, and the outermost panels extending from and overlying the first panels.

3. The diaper of claim 2 wherein the release sheet means comprises a pair of release sheets secured to the back surface of the first panels and generally underlying the first portions of the tape strips, said securement portions of the strips being folded back and attached to the release sheets.

4. A disposable diaper, comprising:
    an absorbent pad assembly having a front surface, a back surface, a pair of side edges, a plurality of longitudinally extending folds defining a box pleat configuration of the diaper having a central panel, a pair of first panels overlying and extending from the central panel, and a pair of outermost panels extending from and overlying the first panels;
    a pair of pressure-sensitive tape strips having a first portion secured to the back surface of the outermost panels adjacent the side edges of the pad assembly, and a securement portion extending from an end of the first portions adjacent said side edges; and
    a pair of release sheets secured to the back surface of the first panels and generally underlying the first portions of the tape strips, said securement portions being folded back adjacent the side edges of the pad assembly and attached to the release sheets to retain the outermost panels in their overlying relationship prior to placement of the diaper.

5. A folded disposable diaper having an inside surface for direction toward an infant and an outside surface for direction away from said infant when the diaper is worn by that infant and comprising: a substantially moisture-impervious backing sheet, a moisture retaining layer adhered to one side of said backing sheet, a pair of adhesive tabs each having a fixed end adhered to a marginal portion of said backing sheet on the side thereof opposite said moisture retaining layer and a free end having a tacky surface on the side thereof adapted to face in the same direction as said diaper inside surface, and a release region on said backing sheet inwardly of and adjacent to each folded-back free end; the free ends of said tabs each being folded back against the respective fixed ends to provide an exposed tacky surface facing in the same direction as said diaper outside surface and each side margin of said diaper being folded against the outside surface of the diaper so as to position the tacky surface on the folded-back free ends in surface-to-surface releasable adherence with said adjacent release coated region; whereby the diaper is held in a folded attitude suitable for storage and from which attitude the diaper can be opened by a pull on said side margin releasing the free end of each of said tabs for use in applying the diaper to said infant.

6. The disposable diaper in accordance with claim 5 wherein said release region is a release coating on the fixed end of each tab and facing in the same direction as the diaper outside surface.

7. The disposable diaper in accordance with claim 5 wherein said release region is a tape segment adhered to said diaper backing sheet and having a release surface facing in the same direction as the diaper outside surface.

8. The disposable diaper in accordance with claim 5 wherein the side margins are folded toward each other with the backing sheet innermost and wherein said adhesive tabs are situated within the resulting fold so that the tacky surfaces of said tab free ends are in contact with adjacent release coated regions.

9. The disposable diaper in accordance with claim 5 wherein the side margins are folded toward each other in a box pleat and wherein said adhesive tabs are situated within the resulting fold so that the tacky surfaces of said tab free ends are in contact with adjacent release coated regions.

10. The disposable diaper in accordance with claim 5 wherein said release region is a tape segment having a release surface facing in the same direction as the diaper outside surface and larger in area than the tacky surface of the adjacent folded-back tab free end.

11. The disposable diaper in accordance with claim 5 wherein each adhesive tab comprises a tape segment having a tacky surface on one side thereof and a release coating on the other side thereof, said tab being folded back on itself about a fold line disposed inwardly from the distal end of the tab about one-third the length of the tab to overly the central one-third of the tab, and the release coating on the innermost one-third of the tab being in contact with the tacky surface on the tab portion overlying the central one-third of the tab.

12. The disposable diaper in accordance with claim 5 wherein each adhesive tab comprises a tape segment having a tacky surface on one side thereof, said tab being folded back on itself about a fold line disposed inwardly from the distal end of the tab about one-half the length of the tab, and the tacky surface on the folded-back portion of the tab being releasably attached to a release surface on the diaper backing sheet.

* * * * *